United States Patent [19]
Zarnowski et al.

[11] Patent Number: 4,892,093
[45] Date of Patent: Jan. 9, 1990

[54] FEMORAL CUTTING GUIDE

[75] Inventors: Alfred J. Zarnowski, North Plainfield, N.J.; Christopher G. Sidebotham, Scotchtown, N.Y.

[73] Assignee: Osteonics Corp., Allendale, N.J.

[21] Appl. No.: 263,687

[22] Filed: Oct. 28, 1988

[51] Int. Cl.⁴ .............................................. A61F 5/04
[52] U.S. Cl. ...................... 606/82; 606/88; 606/96
[58] Field of Search .......... 128/92 VD, 92 YD, 92 V, 128/92 VZ, 92 YV, 92 VS, 91 A, 92 R, 92 VY; 269/368

[56] References Cited

U.S. PATENT DOCUMENTS

| | | | |
|---|---|---|---|
| 4,421,112 | 12/1983 | Mains | 128/92 VY |
| 4,627,425 | 12/1986 | Reese | 128/92 VY |
| 4,664,102 | 5/1987 | Comparetto | 128/92 VY |
| 4,718,413 | 1/1988 | Johnson | 128/92 VW |
| 4,736,737 | 4/1988 | Fargie | 128/92 VY |
| 4,750,481 | 6/1988 | Reese | 128/92 V |
| 4,757,810 | 7/1988 | Reese | 128/92 V |
| 4,773,407 | 9/1988 | Petersen | 128/92 V |

Primary Examiner—Danton D. DeMille
Assistant Examiner—Michael Brown
Attorney, Agent, or Firm—Samuelson & Jacob

[57] ABSTRACT

A cutting guide for guiding a saw blade during the preparation of a femur for the implant of the femoral component of a knee prothesis includes guide surfaces for enabling the cutting of all four of the anterior femoral cut, the posterior femoral cut, the anterior chamfer and the posterior chamfer, fully and completely, with certitude and accuracy, while the cutting guide remains located and secured to the femur in a single position on a transverse surface located along the distal femur.

16 Claims, 3 Drawing Sheets

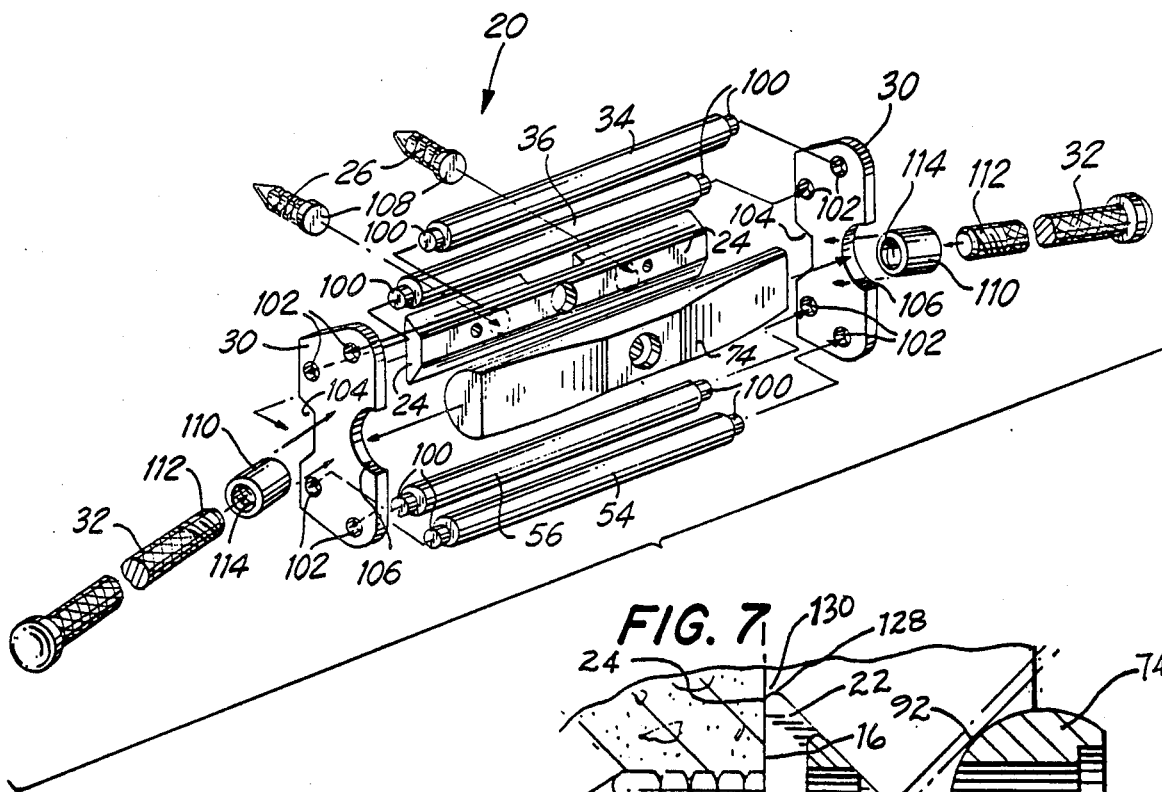
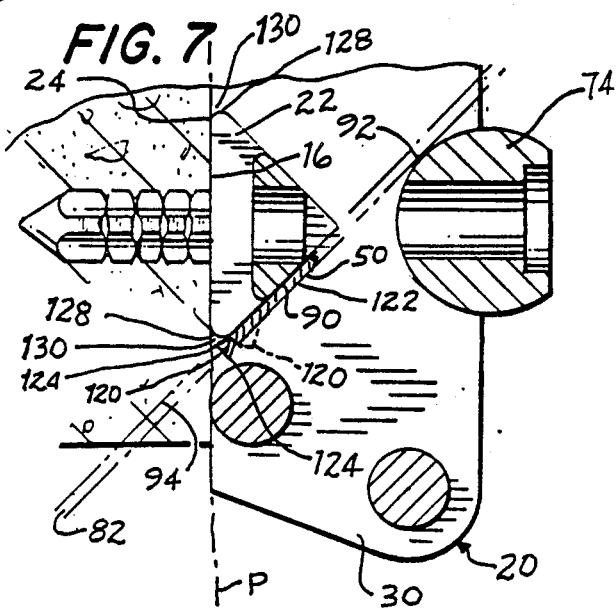
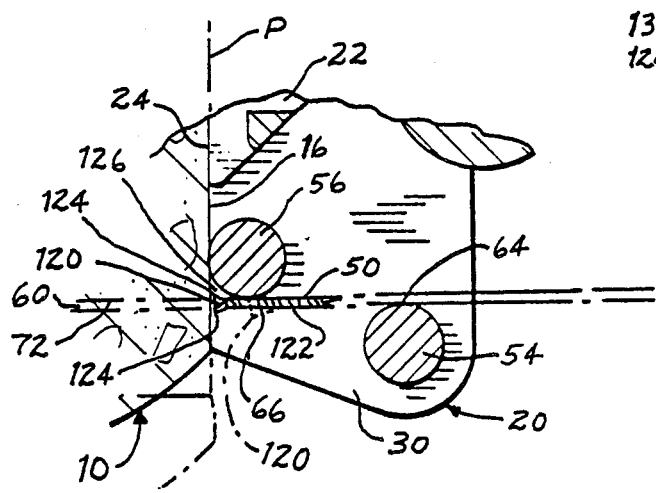
FIG. 7
FIG. 9
FIG. 8

FEMORAL CUTTING GUIDE

The present invention relates generally to the implant of prosthetic joints and pertains, more specifically, to the preparation of the distal femur for the implant of a femoral knee prosthesis, utilizing a cutting guide to assist in establishing the surfaces necessary for locating and securing the prosthesis in place on the femur.

The implant of a prosthetic knee joint requires that the distal femur be prepared to receive the femoral component of the knee prosthesis by cutting the bone of the femur to establish accurately located surfaces against which the femoral knee prosthesis will rest upon implant of the femoral component. Various guides are available to the surgeon for assisting in guiding a saw blade during use of the saw blade to make the cuts which establish the desired surfaces. These guides usually are located and secured upon a transverse surface established initially on the distal femur to provide guide surfaces for guiding the saw blade during the execution of an axially directed anterior femoral cut, an axially directed posterior femoral cut, an anterior chamfer and a posterior chamfer. Currently available guides require either separate guide components secured sequentially to the transverse surface to accomplish the various cuts, or a single guide component which can guide a saw blade through partial execution of the various cuts, with the cuts being completed subsequent to removal of the guide component. Since it is desirable that all of the necessary cuts be established as quickly as possible, concomitant with safety and accuracy, it would be advantageous to have available a cutting guide which enables all of the required cuts to be executed fully and completely with a single cutting guide, without the necessity for the sequential use of a plurality of cutting guides.

The present invention provides a cutting guide which enables the execution of all of the necessary cuts, as outlined above, fully and completely, utilizing only a single cutting guide, and has several objects and advantages, some of which are summarized as follows: Provides a single cutting guide for guiding a saw blade during the execution of the complete anterior femoral cut, posterior femoral cut, anterior chamfer and posterior chamfer during the implant of the femoral component of a prosthetic knee joint; Enhances the speed and accuracy with which all of the aforesaid cuts can be accomplished; Enables all of the aforesaid cuts to be established with an accurately fixed relationship relative to one another, as a result of the placement of all of the saw blade guiding surfaces on a single guide; Minimizes the time required for the completion of all of the aforesaid cuts, while maintaining safety, thereby reducing the overall operating time, to the benefit of the patient and the surgeon; Reduces the possibility of error in the accurate location of the cuts; Is simple and effective in use; Aids in the preservation of the tissue remaining upon completion of the cuts by minimizing any trauma related to the installation and removal of cutting guides; Provides a practical and economical construction which is rugged enough to withstand the rigors of use over a long service life, with the preservation of accuracy and ease of use.

The above objects and advantages, as well as further objects and advantages, are attained by the present invention which may be described briefly as a cutting guide for guiding a saw blade during the preparation of a femur for the implant of a femoral knee prosthesis, the cutting guide enabling guiding of the saw blade for cutting an axially directed anterior femoral cut, an axially directed posterior femoral cut, an anterior chamfer and a posterior chamfer, while the cutting guide remains located on and secured to the femur in a single position on a transverse surface located along the distal femur, the cutting guide comprising: a base member; locating and securing means on the base member for locating and securing the base member on the femur at the transverse surface; opposite side members extending from the base member in an axial direction distally relative to the transverse surface; a first set of guide members extending laterally between the side members and located to delineate transversely opposite boundaries of an axially directed anterior cutting path intercepting the anterior femur, the first set of guide members including opposite guide surfaces spaced apart axially along the anterior cutting path for guiding the saw blade along the anterior cutting path during the anterior femoral cut; a second set of guide members spaced transversely from the first set of guide members, the second set of guide members extending laterally between the side members and located to delineate transversely opposite boundaries of an axially directed posterior cutting path intercepting the posterior femur, the second set of guide members including opposite guide surfaces spaced apart axially along the posterior cutting path for guiding the saw blade along the posterior cutting path during the posterior femoral cut; and a further set of guide members located transversely between the first and second sets of guide members, the further guide members extending laterally between the side members and located for delineating transversely opposite boundaries of an oblique anterior chamfer cutting path and delineating transversely opposite boundaries of an oblique posterior chamfer cutting path, the further guide members including first opposite guide surfaces spaced apart along the oblique anterior chamfer cutting path for guiding the saw blade along the oblique anterior chamfer cutting path during the anterior chamfer cut and second opposite guide surfaces spaced apart along the oblique posterior chamfer cutting path for guiding the saw blade during the posterior chamfer cut; the side members being spaced apart laterally a distance sufficient to provide each of the delineated anterior cutting path, posterior cutting path, anterior chamfer cutting path and posterior chamfer cutting path with a continuous, uninterrupted lateral extent corresponding to the full lateral extent of the respective anterior femoral cut, posterior femoral cut, anterior chamfer and posterior chamfer, whereby the full anterior femoral cut, the full posterior femoral cut, the full anterior chamfer and the full posterior chamfer are accomplished while the cutting guide is located and secured on the femur in the single position on the transverse surface of the distal femur.

The invention will be understood more fully, while still further objects and advantages will become apparent, in the following detailed description of a preferred embodiment of the invention illustrated in the accompanying drawing, in which:

FIG. 7 is a perspective view of component parts of the cutting guide illustrating the construction of the cutting guide;

FIG. 8 is an enlarged fragmentary view of a portion of FIG. 3; and

FIG. 9 is an enlarged fragmentary view of a portion of FIG. 5.

Figure 1:
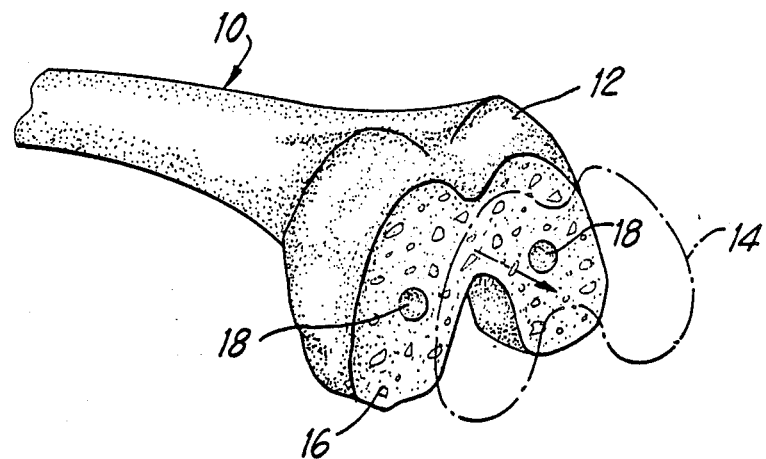
FIG. 1 is a pictorial perspective view of the distal end of a femur, showing an initial step in preparation for the implant of a prosthetic knee joint.

Referring now to the drawing, and especially to FIG. 1 thereof, a femur is illustrated at 10 and is seen to have a distal end 12 which has undergone initial preparation for the implant of a femoral component of a knee prosthesis (not shown) to the extent that a distal portion (shown in phantom at 14) has been removed and a transverse surface 16 has been established at the distal end 12. Transverse surface 16 is planar, and a pair of axially extending holes 18 have been drilled into the bone of the femur 10 for purposes which will be explained below.

Figure 2:
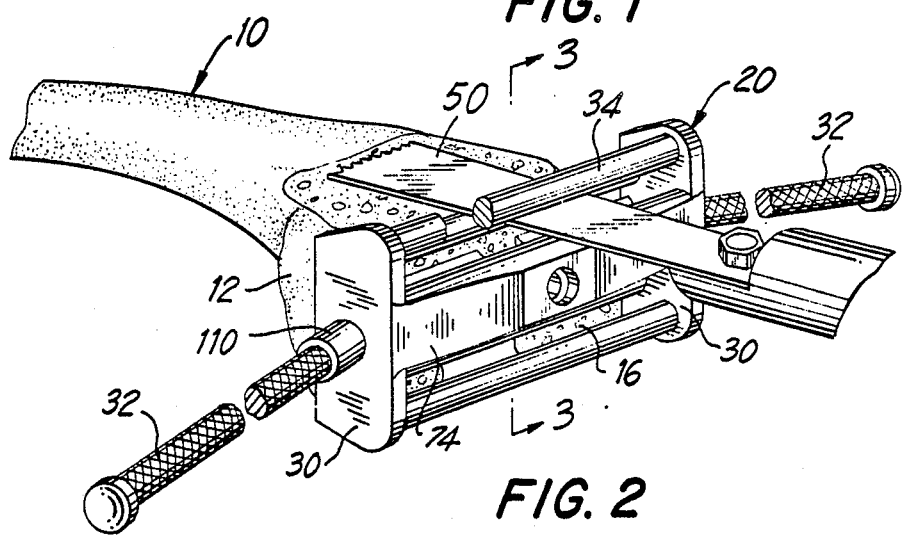
FIG. 2 is a pictorial perspective view showing a cutting guide constructed in accordance with the present invention in use at the distal end of the femur.
Figure 3:
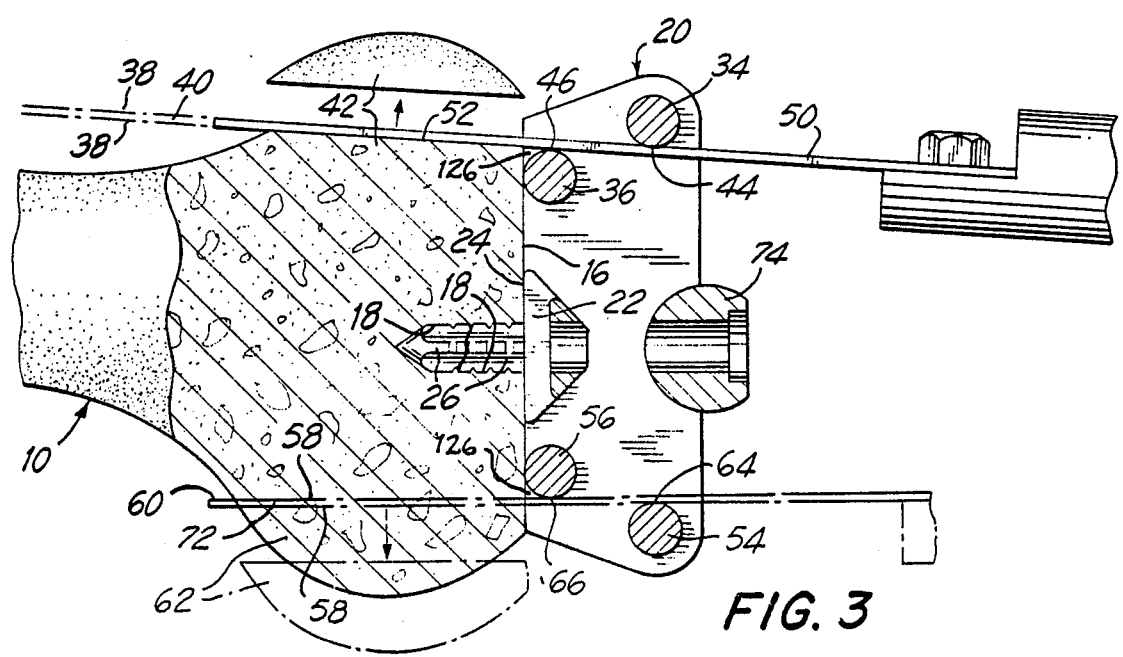
FIG. 3 is an enlarged cross-sectional view taken along line 3—3 of FIG. 2.

Turning now to FIGS. 2 and 3, a cutting guide constructed in accordance with the invention is illustrated at 20 and is secured to the distal end 12 of femur 10. Cutting guide 20 includes a base member 22 having a planar basal surface 24 which is seated upon the transverse surface 16. A pair of laterally spaced apart locating and securing posts 26 are integral with the base member 22 and project in a direction normal to the basal surface 24 to enter the holes 18, which holes 18 are generally complementary to the posts 26 so that the posts 26 cooperate with the holes 18 to locate and secure the cutting guide 20 at a predetermined position on the distal femur. A pair of opposite side members 30 are integral with the base member 22 and extend from the base member 22 in an axial direction distally relative to the transverse surface 16. A pair of handgrips 32 extend laterally outwardly in opposite directions from the side members 30 and facilitate manipulation of the cutting guide 20 during installation and removal of the cutting guide 20, as well as during use of the cutting guide 20.

A first set of guide members is shown as a pair of guide members in the form of a first cylindrical bar 34 and a second cylindrical bar 36, both bars 34 and 36 extending laterally, parallel to one another, from one to the other of the side members 30. The bars 34 and 36 are located to delineate transversely opposite boundaries 38 of an axially directed anterior cutting path 40 intercepting the anterior femur 42, the bars 34 and 36 including opposite guide surfaces 44 and 46 adjacent the corresponding opposite boundaries 38 and spaced apart axially along the anterior cutting path 40. Thus, a saw blade 50 inserted between the guide surfaces 44 and 46 and urged simultaneously against both guide surfaces 44 and 46 follows the anterior cutting path 40 and executes the anterior femoral cut 52 with certitude and accuracy. A second set of guide members is shown as a pair of guide members in the form of a third cylindrical bar 54 and a fourth cylindrical bar 56, both bars 54 and 56 extending laterally, parallel to one another, from one to the other of the side members 30. The bars 54 and 56 are located to delineate transversely opposite boundaries 58 of an axially directed posterior cutting path 60 intercepting the posterior femur 62, the bars 54 and 56 including opposite guide surfaces 64 and 66 adjacent the corresponding opposite boundaries 58 and spaced apart axially along the posterior cutting path 60. Insertion of the saw blade 50 between the guide surfaces 64 and 66 and the simultaneous urging of the saw blade 50 against both guide surfaces 64 and 66 assures that the saw blade follows the posterior cutting path 60 and executes the posterior femoral cut 72 with certitude and accuracy.

Figure 4:
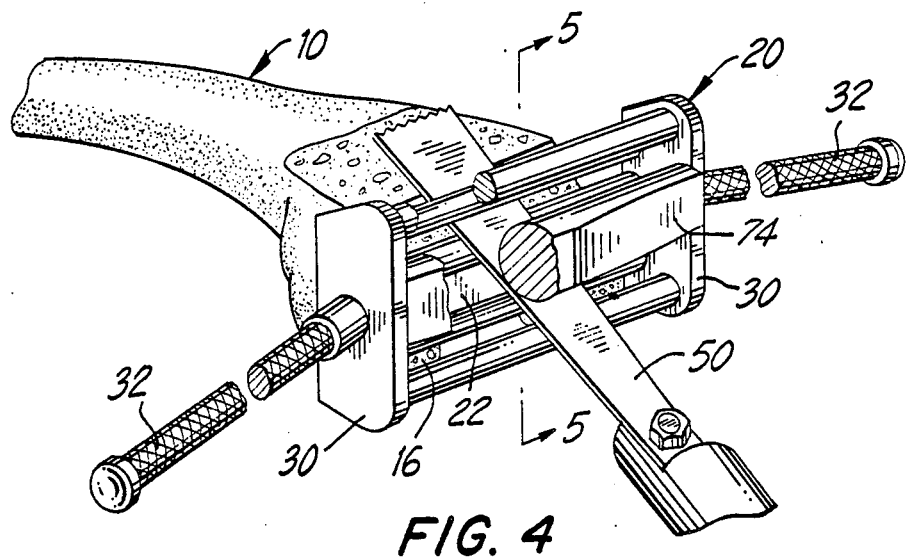
FIG. 4 is a view similar to that of FIG. 2, but illustrating the execution of another cut.
Figure 5:
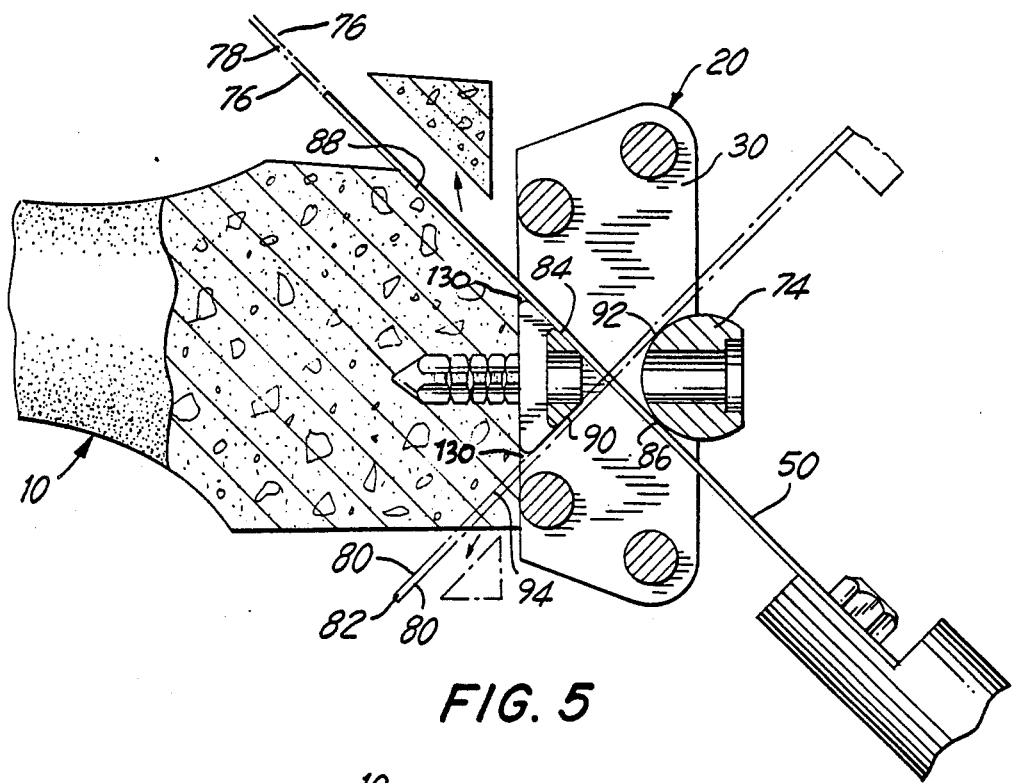
FIG. 5 is an enlarged cross-sectional view taken along line 5—5 of FIG. 4.

A further set of guide members is provided by a pair of guide members in the form of base member 22 and a cross-bar 74, both of which are located transversely between the first and second sets of guide members and extend laterally between the side members 30, from one side member 30 to the other side member 30. As seen in FIGS. 4 and 5, base member 22 and cross-bar 74 are located so as to delineate the opposite boundaries 76 of an oblique anterior chamfer cutting path 78, and the opposite boundaries 80 of an oblique posterior chamfer cutting path 82. Opposite guide surfaces 84 and 86 are located on the base member 22 and the cross-bar 74, respectively, and are spaced apart along the oblique anterior chamfer cutting path 78 for guiding the saw blade 50 along the oblique anterior chamfer cutting path 78, when the saw blade 50 is inserted between the base member 22 and the cross-bar 74 and urged against the guide surfaces 84 and 86 as shown, so that the anterior chamfer 88 is executed with certitude and accuracy. Likewise, opposite guide surfaces 90 and 92 are located on the base member 22 and the cross-bar 74, respectively, and are spaced apart along the oblique posterior chamfer cutting path 82 for guiding the saw blade 50 along the oblique posterior chamfer cutting path 82, when the saw blade 50 is inserted between the base member 22 and the cross-bar 74 and urged against the guide surfaces 90 and 92 as shown in phantom in FIG. 5, so that the posterior chamfer 94 is executed with certitude and accuracy. Guide surfaces 84 and 90 are essentially flat and extend generally parallel to the respective anterior and posterior chamfer cutting paths 78 and 82.

Figure 6:
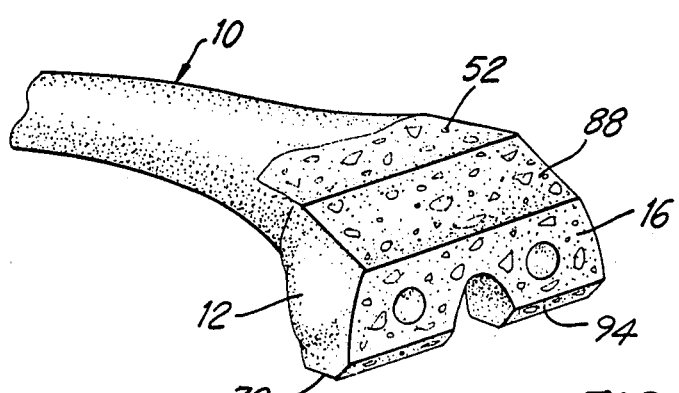
FIG. 6 is a pictorial perspective view similar to FIG. 1, but showing a fully-prepared distal femur.

It is noted that the side members 30 are spaced apart laterally a distance sufficient to provide each of the delineated anterior cutting path 40, posterior cutting path 60, anterior chamfer cutting path 78 and posterior chamfer cutting path 82 with a continuous, uninterrupted lateral extent corresponding to the full lateral extent of the respective anterior femoral cut 52, posterior femoral cut 72, anterior chamfer 88 and posterior chamfer 94, whereby the full anterior femoral cut 52, the full posterior femoral cut 72, the full anterior chamfer 88 and the full posterior chamfer 94 are accomplished while the cutting guide 20 is secured to the femur 10 in the single illustrated position on the transverse surface 16 of the distal femur. Subsequent to the completion of all of the four cuts set forth above, the cutting guide 20 is removed from the femur 10, and the preparation of the distal femur is complete, as illustrated in FIG. 6.

Turning now to FIG. 7, cutting guide 20 preferably is constructed by assembling discreet individual component parts, as by welding the individual component parts into an integrated assembly. Thus, each of the cylindrical bars 34, 36, 54 and 56 are joined to the side members 30, as by welding at the respective ends of the cylindrical bars. Likewise, the base 22 and the cross-bar 74 are joined to the side members 30, as by welding at the respective ends thereof. In order to attain accuracy in the relative location of the component parts in the completed assembly, cylindrical bars 34, 36, 54 and 56 include projections 100 at the ends thereof, and the side members 30 include complementary recesses 102 into which the projections 100 are fitted prior to welding. For the same purpose, the ends of base 22 and cross-bar 74 are fitted into respective notches 104 and 106 in the side members 30, the notches 104 and 106 being complementary to the respective ends of the base 22 and the cross-bar 74. Posts 26 include integral pads 108 which are fitted into complementary recesses (not shown) in base 22 for accurate location of the posts 26 prior to welding the posts in place. Handgrips 32 are received within respective collars 110 affixed to the side members 30, as by welding, and are selectively attached to and detached from the collars 110 by complementary threaded elements 112 and 114. Preferably, all of the component parts are placed in a fixture (not shown) prior to joining the parts, to further assure accuracy in the location of the guide surfaces provided by the laterally extending component parts, relative to the basal surface 24, with concomitant accuracy in the location of the guide surfaces relative to the transverse surface 16 of the distal femur. Thus, the integrated assembly provides the necessary accuracy in an economically constructed cutting guide.

Referring now to FIGS. 8 and 9, it is noted that saw blade 50 is of the type which includes teeth 120 offset from the remainder 122 of the saw blade, as shown at offset tooth portions 124. As an offset tooth portion 124 engages a corresponding guide surface, illustrated at 66 in FIG. 8 and at 90 in FIG. 9, the saw blade 50 will be moved out of the respective cutting path 60 and 82, as illustrated in phantom, so as to pass over the corresponding bar 56 or base member 22. In order to assure that the saw blade 50 is aligned accurately with the appropriate cutting path upon entering the bone of the femur 10 at the commencement of a cut, as illustrated in full lines, clearance means are provided so that the offset tooth portion 124 will clear the respective guide surface just prior to entering the distal femur, when the teeth 120 are juxtaposed with the transverse surface 16 on the femur, and the saw blade 50, and the teeth 120 thereof, will be located within the corresponding delineated cutting path. Thus, as seen in FIG. 8, the bar 56 is juxtaposed with the transverse surface 16 and the cylindrical configuration of bar 56 establishes a gap 126 along the cutting path 60 between the guide surfaces provided by the bars and the plane P which extends along the transverse surface 16 and represents the basal plane of basal surface 24, which gap 126 accommodates the offset tooth portion 124 to enable the saw blade 50, and the teeth 120 thereof, to be located precisely within the delineated cutting path 60 at the commencement of the corresponding posterior femoral cut 72 for accuracy in the completed cut. Likewise, a small radius is provided at 128 on the base member 22 to establish a gap 130 juxtaposed with the basal surface 24, along the cutting path 82 between the guide surface 90 and the plane P, for accommodating the offset tooth portion 124 and assuring accuracy at the commencement of the posterior chamfer cut 94. Corresponding gaps 126 and 130 are located similarly in connection with the guide surfaces 46 and 84, as seen in FIGS. 3 and 5.

It will be seen that the cutting guide 20 provides a single component which can be placed on the transverse surface 16 of the distal femur for accomplishing the guiding of a saw blade for the execution of all four of the cuts, in full, as required for the implant of the femoral component of a knee prosthesis. The cuts are accomplished with relative ease and with great accuracy, and can be completed more quickly, with safety.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. A cutting guide for guiding a saw blade during the preparation of a femur for the implant of a femoral knee prosthesis, said cutting guide enabling guiding of said saw blade for cutting an axially directed anterior femoral cut, an axially directed posterior femoral cut, an anterior chamfer and a posterior chamfer, while said cutting guide remains located and secured to the femur in a single position on a transverse surface located along the distal femur, said cutting guide comprising:

a base member;

locating and securing means on said base member for locating and securing said base member on the femur at said transverse surface;

opposite side members extending from said base member in an axial direction distally relative to said transverse surface;

a first set of guide members extending laterally between said side members and located to delineate transversely opposite boundaries of an axially directed anterior cutting path intercepting the anterior femur, said first set of guide members including opposite guide surfaces spaced apart axially along said anterior cutting path for guiding said saw blade along said anterior cutting path during the anterior femoral cut;

a second set of guide members spaced transversely from said first set of guide members, said second set of guide members extending laterally between said side members and located to delineate transversely opposite boundaries of an axially directed posterior cutting path intercepting the posterior femur, said second set of guide members including opposite guide surfaces spaced apart axially along said posterior cutting path for guiding said saw blade along said posterior cutting path during the posterior femoral cut; and a further set of guide members located transversely between said first and second sets of guide members, said further guide members extending laterally between said side members and located for delineating transversely opposite boundaries of an oblique anterior chamfer cutting path and delineating transversely opposite boundaries of an oblique posterior chamfer cutting path, said further guide members including first opposite guide surfaces spaced apart along said oblique anterior chamfer cutting path for guiding said saw blade along said oblique anterior chamfer cutting path during the anterior chamfer cut and second apposite guide surfaces spaced apart along said oblique posterior chamfer cutting path for guiding said saw blade during the posterior chamfer cut;

said side members being spaced apart laterally a distance sufficient to provide each of said delineated anterior cutting path, posterior cutting path, anterior chamfer cutting path and posterior chamfer cutting path with a continuous, uninterrupted lateral extent corresponding to the full lateral extent of the respective anterior femoral cut, posterior femoral cut, anterior chamfer and posterior chamfer, whereby the full anterior femoral cut, the full posterior femoral cut, the full anterior chamfer and the full posterior chamfer are accomplished while said cutting guide is located and secured on the femur in the single position on said transverse surface of the distal femur.

2. The invention of claim 1 wherein said first set of guide members comprises a pair of guide members, and said opposite guide surfaces of said first set of guide members are located on said pair of guide members.

3. The invention of claim 1 wherein said second set of guide members comprises a pair of guide members, and said opposite guide surfaces of said first set of guide members are located on said pair of guide members.

4. The invention of claim 1 wherein said further set of guide members comprises a pair of guide members, and said first and second opposite guide surfaces are located on said pair of guide members.

5. The invention of claim 1 wherein guide members of at least one of said first set of guide members and said second set of guide members are cylindrical bars.

6. The invention of claim 1 wherein said guide members of said first set of guide members and said second set of guide members are cylindrical bars.

7. The invention of claim 1 wherein one of said first opposite guide surfaces of said further set of guide members is essentially flat and generally parallel to said anterior chamfer cutting path.

8. The invention of claim 1 wherein one of said second opposite guide surfaces of said further set of guide members is essentially flat and generally parallel to said posterior chamfer cutting path.

9. The invention of claim 1 wherein one of said first opposite guide surfaces of said further set of guide members is essentially flat and generally parallel to said anterior chamfer cutting path and one of said second opposite guide surfaces of said further set of guide members is essentially flat and generally parallel to said posterior chamfer cutting path.

10. The invention of claim 9 wherein said further set of guide members comprises a pair of guide members, and said first and second opposite guide surfaces are located on said pair of guide members.

11. The invention of claim 1 wherein at least some of said guide members are formed from discrete components and are joined with said side members such that said cutting guide is an integral assembly of said side members and said guide members.

12. In a cutting guide for guiding a saw blade during the preparation of a femur for the implant of a femoral knee prosthesis, said cutting guide enabling guiding of said saw blade for the execution of a cut such as any one of an axially directed anterior femoral cut, an axially directed posterior femoral cut, an anterior chamfer cut and a posterior chamfer cut, while said cutting guide is placed on a transverse surface located along the femur, said saw blade having teeth offset relative to the remainder of said saw blade and establishing offset tooth portions, said cutting guide including a base member at least a portion of which lies in a basal plane coincident with said transverse surface, locating and securing means on said base member for locating and securing said base member on the femur, with said portion of said base member against said transverse surface, and at least one guide member juxtaposed with said transverse surface, when said cutting guide is Placed on the transverse surface, said guide member including a guide surface for delineating a cutting path intercepting the femur, along which cutting path said saw blade is guided during the execution of the cut, the improvement comprising:

clearance means between said guide surface and said basal plane for accommodating said offset tooth portions of said saw blade when said offset tooth portions are juxtaposed with said transverse surface, with said saw blade guided along said cutting path, so as to enable location of said saw blade and said teeth thereof within said cutting path at the commencement of the corresponding cut.

13. The invention of claim 12 wherein clearance means includes a gap along said cutting path between said guide surface and said basal plane.

14. The invention of claim 12 wherein said base member includes a basal surface at least a portion of which is placed against said transverse surface when said base member is located and secured on the femur, and said clearance means is located on said base member and is juxtaposed with said basal surface of said base member.

15. The invention of claim 14 wherein said portion of said basal surface is planar.

16. The invention of claim 15 wherein said clearance means includes a gap along said cutting path between said guide surface and said basal plane.

* * * * *